United States Patent [19]
Weber

[11] Patent Number: 4,505,271
[45] Date of Patent: Mar. 19, 1985

[54] APPLIANCE FOR THE RELIEF OF ARTHRITIC PAIN

[76] Inventor: Arthur Weber, 429 Lake View Dr., Bonaventure Bldg., 83, Apt. 202, Ft. Lauderdale, Fla. 33326

[21] Appl. No.: 594,061

[22] Filed: Mar. 28, 1984

[51] Int. Cl.$^3$ ............................................. A61F 13/00
[52] U.S. Cl. ................................... 128/157; 128/165; 128/402
[58] Field of Search ................. 128/82, 402, 165, 157, 128/82.1, 155, 156

[56] References Cited

U.S. PATENT DOCUMENTS

| | | | |
|---|---|---|---|
| 3,421,503 | 1/1969 | Kaplan | 128/157 |
| 3,600,717 | 8/1971 | McKeehan | 128/157 |
| 3,902,503 | 9/1975 | Gaylord, Jr. | 128/165 |
| 4,084,586 | 4/1978 | Hettick | 128/157 |

*Primary Examiner*—John D. Yasko
*Attorney, Agent, or Firm*—Sughrue, Mion, Zinn, Macpeak, and Seas

[57] ABSTRACT

The invention relates to an appliance for the treatment and relief of arthritic pain. The apparatus may be embodied in many shapes and forms depending upon the body part to be treated, but is generally comprised of a laminar construction of plural elastic fiber layers, which are held together at their longitudinal edges by elastic joints. Lateral edges of the layers are held together by strength joints, which are positioned substantially adjacent to each other when the appliance is wrapped around the body part to be treated and is secured in place.

8 Claims, 8 Drawing Figures

APPLIANCE FOR THE RELIEF OF ARTHRITIC PAIN

BACKGROUND OF THE INVENTION

The present invention relates to a device or appliance which has been found to alleviate arthritic pain by the application of uniform compression to the affected area, combined with an insulative, heat retentive effect. Prior art devices of a construction similar to the present device have been known in the athletic and surgical arts, and generally consists of a web or the like of elastic material, such as the well-known Ace bandage or variants thereof. For example, U.S. Pat. No. 663,749 to Gorse discloses a knee brace made of stretchable fabric formed into front and rear pieces and having a different weave for the fore and aft portions of the affected body area, typically a knee or elbow joint as mentioned. Such a construction provides different compression at the front and rear sides of the joint, primarily so that the bandage will more easily remain in place, or "ride" with the wearer.

There are many known-devices of linear or tubular construction which are adapted to be used as supports for various body joints such as knees and elbows. Among such devices, there are known tubular bandages such as that disclosed by Rosenfield in U.S. Pat. No. 3,306,288, and linear devices suitable for wrapping about the affected area as disclosed by e.g., U.S. Pat. No. 3,942,525 to Dragan; U.S. Pat. No. 3,563,238 to McGuire and U.S. Pat. No. 3,804,084 to Lehman. In general, these devices are not designed for heat retention or for applying uniform compression to the affected area. When such a bandage is concerned with allowing flexure of the joint, it is typical to provide means for allowing the bandage to "ride" with the joint without sagging or being displaced from the joint. In such cases, as exemplified by the previously noted patent to Gorse, uniform compression and heat retention are sacrificed for the ability of the bandage to be more easily worn by the wearer. In other cases, it is desired to make the affected joint substantially immobile, such as in the case of bone breakage or muscle or ligament damage. In such devices, compression is a key element in the design of the device, although flexibility is generally sacrificed and heat retention is not a factor.

Devices of the type disclosed by U.S. Pat. No. 4,370,978 to Palumbo provide suitable compression to the affected area, but this compression is not uniform inasmuch as it is desired to support particular muscular masses. Braces such as that disclosed by this patent are useful only for one specific bodily area, as they are specifically designed with the musculature in this region in mind. Further, bandages of this type do not provide any heat retentive effect except of an incidental nature.

U.S. Pat. No. 3,892,239 to Masso Remiro describes a covering element comprised of a layer of ribbed, knitted fabric, which is covered by a thin, non-permeable layer of rubber. The rubber material forms a vapor barrier, while the ribbing in the knitted material allows for the slow passage of air therethrough and creates a massaging action. Although the device claims a degree of body heat retention, the skin is still in contact with the air through the channels formed between the ribs. Also, the rubber layer does not permit the evaporation of moisture, which is thus accumulated on the inside of the bandage.

The Kaplan patents, U.S. Pat. Nos. 3,115,879 and 3,421,503, relate to support devices generally made up of a plurality of elastic bodies arranged in side by side fashion and stitched together so as to allow expansion in the length direction of the support. The individual elastic webs forming the supports are stretchable in their longitudinal direction, but not in their width direction, and the stitching holding the webs together is likewise arranged so as to permit longitudinal expansion but limit the formatio of gaps between webs in the width direction. The space between adjacent webs is left open, and one or more openings in the device may be created in order to allow easy flexure of the joint in the region of the affected area. No particular heat retentive effect is attained or promoted by these devices.

SUMMARY OF THE INVENTION

In view of the foregoing various deficiencies of the prior art, it is a primary object of the present invention to provide an elastic appliance particularly for body joints afflicted with arthritis, which appliance is capable of exerting a uniform compressive force upon the joint.

It is a further object of the invention to provide an elastic appliance of the type described above, which further promotes the retention of body heat in the afflicted area by the employment of an insulative, laminar structure.

It is a still further object of the present invention to provide an appliance for the relief of arthritic pain as above described, wherein stitching of the appliance is carried out in a manner such that flexure is permitted in areas subjected to elastic deformation, while strength is maintained at regions of the appliance requiring the same.

BRIEF DESCRIPTION OF THE DRAWINGS

The additional objectives and characterizing features of the invention and its form of application will become apparent from the following detailed description, taken in conjunction with the accompanying drawings, in which.

DETAILED DESCRIPTION OF THE PREFERRED EMBODIMENTS

Figure 1:
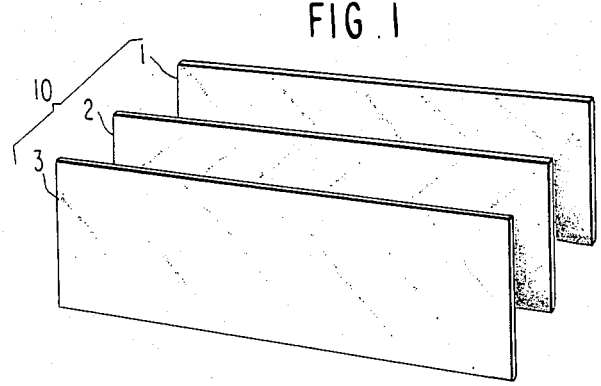
FIG. 1 is a perspective view showing the parts of the elastic appliance prior to assembly.

The device according to the present invention may be embodied in any of a number of appliances for use with specific body parts. As is commonly known, particular body joints are most commonly afflicted with arthritis, especially the knees, elbows and fingers. Accordingly, appliances for use with the knee and with the fingers are disclosed herein, it being understood that the same principles apply to the construction of apparatuses for use on the wrists, elbows, back, and other areas which may be afflicted with arthritis. Referring now to FIG. 1, a first embodiment of the present invention is shown in schematic, unassembled form. The main body of the appliance is formed of three layers of elastic material, which may be a woven textile fabric of the type generally known in the art. In a preferred embodiment of the invention, the elastic fabric is of the type commonly used in the well-known Ace bandage. The material is capable of stretching in a longitudinal direction to approximately 180% of its normal length. For a knee application, the layers of material shown in FIG. 1 may have unbiased dimensions on the order of 4 inches by 12 inches, the material being stretchable to approximately 20 inches in length.

Figure 2:
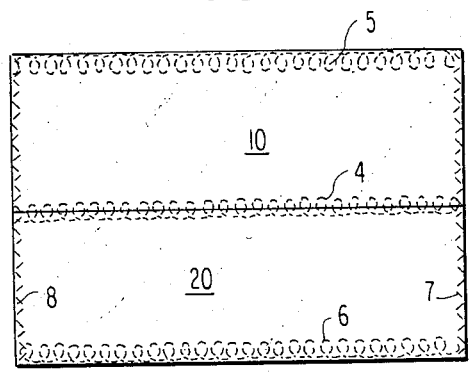
FIG. 2 is a plan view of the present invention, embodied in a knee bandage, showing one step in the manner of construction of the appliance and the stitching of the same.

For a knee application, the three layers 1, 2 and 3 shown in FIG. 1 are laid atop one another to form a laminar structure 10, and two such laminar structures (10, 20) are placed in side by side relation. FIG. 2 shows how two such laminar structures are connected to each other, as well as how the layers 1-3 of each laminar structure are themselves connected. In particular, in the length direction of the appliance, the center boundary 4 between the two laminar structures is connected by means of oval stitching. This type of stitching allows the appliance to be stretched as the knee joint is flexed. Similar stitched joints 5 and 6 are formed along the longitudinal edge of the appliance, and serve to hold the individual layers of the laminate together. The center joint 4 serves both to hold the individual laminae 1-3 together and to connect the two laminar structures 10, 20 together.

The side or lateral edgess of the appliance are joined by stitching 7, 8. This stitched joint is generally formed as a machine made zig-zag stitch. Whereas the oval stitch allows substantial stretching, the zig-zag stitch lends strength to the appliance, which is particularly needed at the lateral edges thereof.

Figure 3:
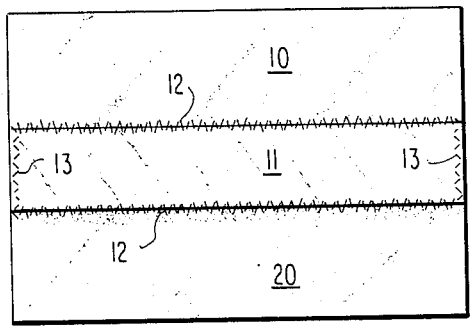
FIG. 3 is a plan view illustrating a further step in the construction of the device.

Next, as seen in FIG. 3, a center strip 11 is laid atop the construction shown in FIG. 2 in a manner such that the center joint 4 lies underneath the center thereof. (the stitching shown in FIG. 2 is not illustrated in FIG. 3 for purposes of drawing clarity). As shown in FIG. 3, the center bandage 11 is approximately one-half the width of an individual laminated structure 10, 20, and consists of a single layer of elastic fabric material.

After being disposed in the manner indicated above, the entire appliance is substantially stretched, and the elastic textile layer 11 is then sewn thereto along seams 12. The seams 12 are sewn with a zig-zag stitch, which lends strength to the appliance in this area. Since the appliance is stretched when stitched, the resulting stitched joint lends strength to the appliance while also allowing a large degree of flexibilitly similar to the oval stitching described above. Stitched joints 14 along the side edges of the appliance are also formed using zig-zag stitching. However, these joints are not formed while the appliance is being stretched. Therefore, these joints have strength and flexibility characteristics similar to the joints 7 and 8 shown in FIG. 2.

Figure 4:
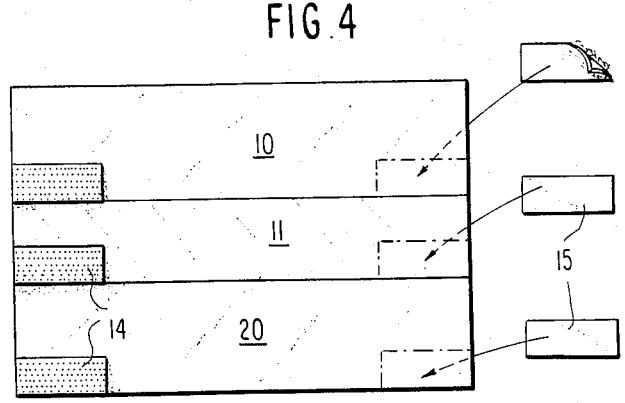
FIG. 4 illustrates the manner of connection of Velcro fasteners to the appliance shown in FIG. 3.

The composite structure is shown in FIG. 4, with the above stitched joints not being illustrated for purposes of clarity.

The device shown in FIG. 4 has dimensions of approximately 8 inches by 12 inches for a knee application.

Of course, in order to use the device, fasteners are necessary to hold the appliance in position covering the affected area. It is particularly preferred to use Velcro-type hook and loop fastener means for this purpose. As indicated in FIG. 4, three members 14 of hook (or loop) fabric are machine sewn on the outwardly facing surface of the appliance. These strips of material measure approximately 1 inch by $2\frac{1}{2}$ inches for the application illustrated, and are positioned at the upper corner of the laminate 10, the lower corner of the laminate 20 and a corner of the center elastic layer 11.

Similarly sized and shaped elements 15 of loop (or hook) fabric are sewn to the backside of the appliance as indicated by the arrows in FIG. 4. The placement of the elements 15 is such that they will overlap the elements 14 when the appliance is wrapped around the knee joint. The length of the Velcro fastener in the longitudinal direction allows for latitude in the amount of compression applied to the joint, and for persons of different sizes. The elements 15 are also machine sewn in the same manner as elements 14.

The apparatus as described above has been found to obtain new and surprising results in the treatment of arthritic pain. Although the mechanism by which the appliance operates is not completely known, it is considered that the laminar structure of the appliance provides insulation to the joint which allows the temperature of the same to be slightly raised due to the retention of body heat. The fabric material of the appliance is inherently breathable, which contributes to the evaporation of perspiration or the like without a substantial loss in heat retention. The insulative effect is primarily due to the laminar structure of the device and the texture and construction of the elastic material used, which creates pockets of warm air adjacent the skin, which air only slowly escapes to the surface of the appliance, carrying moisture therewith.

It is also considered that the compressive stress exerted by the appliance, when taken in conjunction with the insulative or heat retentive effect noted above, assists in the alleviation of pain due to arthritis. The construction of the appliance allows a uniform compression to be radially inwardly applied to the entire joint and the particular stitching employed serves to assist the achievement of uniform compression rather than hinder the same. It is believed that the retention of body heat in the affected area allows a local temperature rise around the affected joint, which, in combination with uniform compression, serves to alleviate arthritic pain. It has been found in limited tests that a one to three week period of wearing the appliance of the invention over an affected joint will serve to alleviate the arthritic pain in this joint.

A second embodiment of the present invention will now be described, with reference to FIGS. 5 and 6. In these Figures, the present invention is embodied in the form of a finger appliance.

Figure 5:
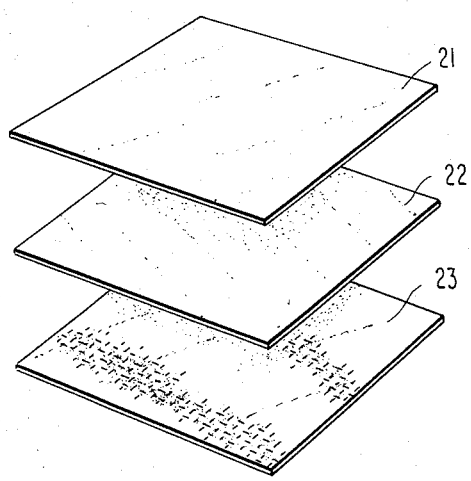
FIG. 5 is a perspective view illustrating the parts of the present invention, as embodied in a finger appliance, prior to assembly.

As shown in FIG. 5, the appliance is constructed of a laminate 30 comprised of three layers 21-23. Layers 21 and 22 are formed of elastic textile material of the same type described in conjunction with the first embodiment. The third layer 23, which will be the innermost layer in the finished device, may either be made of a third elastic textile layer or of a Velox material. All three layers are of the same size, about $2\frac{1}{2}$ inches square in this embodiment.

Figure 6A:
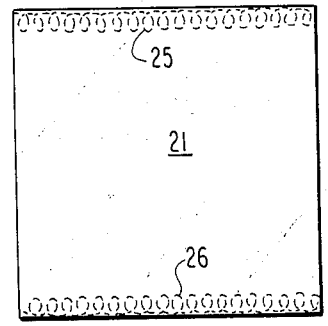
FIGS. 6A through 6C illustrate steps in the construction of the finger appliance.
Figure 6B:
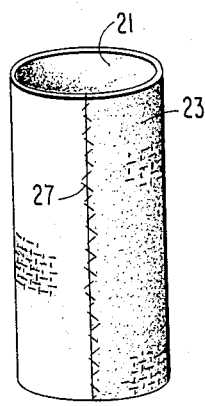
Figure 6C:
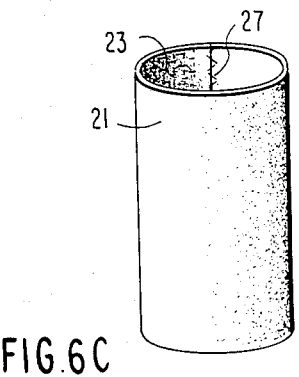

As seen in FIG. 6A, the longitudinal edges of the laminate are joined to form stitched joints 25, 26, which are formed using oval stitching. The laminate is now rolled into the form of a cylinder and sewn together with a strength stitch of zig-zag configuration to form a joint 27. As shown in FIG. 6B, the cylindrical device is joined such that the layer 23 of Velox is toward the outside. The device is then inverted as shown in FIG. 6C to form the final product. The resulting appliance is most commonly worn over the center joint of each affected finger. For different sized fingers, the appliance may be formed in several sizes or may be equipped with adjustable fastening means.

The properties of the apparatus of FIG. 6C are quite similar to those of the knee appliance described above. The oval stitched joints 25, 26 allow stretchability in the primary elastic direction of the laminate, while the zig-zag stitching forms a strength bond holding the longitudinal ends of the appliance together. The construction shown in FIG. 6B allows the finger joint to be insulated and thus heated by retained body heat, while maintaining the same under a uniform and constant compression. Limited tests conducted with the finger appliances of FIG. 6C have obtained similar surprising results as described above, for the same reasons.

It is believed that the apparatus according to the invention achieves several beneficial results not obtained with the use of prior art devices. The appliance is by and large adjustable and capable of fitting several sizes, while eliminating the use of difficult pins, clips, etc. for adjustability. The device of the invention is also hypoallergenic and launderable and does not lose its effectiveness with continued use.

Although only two embodiments of the appliance according to the invention have been described in the foregoing, numerous modifications and adaptations of the inventive device may be made without departing from the spirit and scope of the invention, as defined by the following claims.

I claim:

1. An appliance for the relief of arthritic pain, comprising;
a plurality of layers of elastic textile material, each stretchable in the longitudinal direction thereof and disposed in face-to-face surface contact with one another, said layers of material being joined by stitching free edges thereof in order to form a laminar structure having longitudinal and lateral edges, said layers being joined with flexible joints along the length of said longitudinal edges and with at least one stretch joint along the length of said lateral edges, and means for securing said lateral edges at least proximate one another while encircling an afflicted body part, said layers of elastic textile material being constructed so as to allow a uniform compression to be applied to said body part, and said layers of elastic textile material being sufficient in number to provide for the retention of body heat in the area of said body part.

2. An appliance as claimed in claim 1, wherein said flexible joints comprise oval-stitched joints.

3. An appliance as claimed in claim 1, wherein said strength joints comprise machine sewn joints.

4. An appliance as claimed in claim 1, wherein said securing means comprises at least one hook and loop type fastener.

5. An appliance as claimed in claim 1, wherein said securing means comprises a strength joint.

6. An appliance as claimed in claim 1, wherein at least three layers of said elastic textile material make up said laminate.

7. An appliance as claimed in claim 1, wherein said appliance comprises a pair of said laminar structures joined in side-by-side relationship by an elastic joint, said elastic joint being covered by a further layer of elastic textile material joined to said two laminar structures by longitudinal pre-stretched strength joints.

8. An appliance as claimed in claim 1, wherein said elastic textile material is a breathable material, said appliance being constructed so as to completely enclose said body part.

* * * * *